(12) United States Patent
Scavone et al.

(10) Patent No.: US 9,731,042 B2
(45) Date of Patent: *Aug. 15, 2017

(54) ABSORBENT ARTICLE COMPRISING COMPLEXED OR ENCAPSULATED REACTIVE COMPOUNDS

(71) Applicant: The Procter & Gamble Company, Cincinnati, OH (US)

(72) Inventors: Timothy Alan Scavone, Loveland, OH (US); Misael Omar Aviles, Cincinnati, OH (US); Brian Francis Gray, Cincinnati, OH (US); Peter Christopher Ellingson, Symmes Township, OH (US); Dean Larry Duval, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/308,757

(22) Filed: Jun. 19, 2014

(65) Prior Publication Data

US 2014/0377207 A1    Dec. 25, 2014

Related U.S. Application Data

(60) Provisional application No. 61/836,782, filed on Jun. 19, 2013.

(51) Int. Cl.
| | |
|---|---|
| A61L 15/46 | (2006.01) |
| A61L 15/20 | (2006.01) |
| A61L 15/28 | (2006.01) |
| A61F 13/84 | (2006.01) |

(52) U.S. Cl.
CPC .......... *A61L 15/46* (2013.01); *A61F 13/8405* (2013.01); *A61L 15/20* (2013.01); *A61L 15/28* (2013.01); *A61L 2300/216* (2013.01); *A61L 2300/232* (2013.01); *A61L 2300/62* (2013.01); *A61L 2300/802* (2013.01)

(58) Field of Classification Search
CPC ....................... A61F 13/00063; A61L 2300/62
See application file for complete search history.

(56) References Cited

U.S. PATENT DOCUMENTS

| | | |
|---|---|---|
| 4,540,721 A | 9/1985 | Staller |
| 4,973,422 A | 11/1990 | Schmidt |
| 5,331,015 A | 7/1994 | DesMarais et al. |
| 5,387,207 A | 2/1995 | Dyer et al. |
| 5,543,157 A | 8/1996 | Trinh et al. |
| 5,550,167 A | 8/1996 | DesMarais |
| 5,571,782 A | 11/1996 | Trinh et al. |
| 6,024,943 A | 2/2000 | Ness et al. |
| 6,042,792 A | 3/2000 | Shefer et al. |
| 6,051,540 A | 4/2000 | Shefer et al. |
| 6,458,754 B1 | 10/2002 | Velazquez et al. |
| 6,531,444 B1 | 3/2003 | Shefer et al. |
| 7,316,994 B2 | 1/2008 | Jordan et al. |
| 7,365,043 B2 | 4/2008 | Baker et al. |
| 8,187,580 B2 | 5/2012 | Dykstra et al. |
| 2004/0091445 A1 | 5/2004 | Dykstra et al. |
| 2005/0124530 A1 | 6/2005 | Creutz et al. |
| 2005/0143282 A1 | 6/2005 | Creutz et al. |
| 2006/0003913 A1 | 1/2006 | Boutique et al. |
| 2007/0207942 A1 | 9/2007 | Creutz et al. |
| 2008/0213191 A1 | 9/2008 | Scavone et al. |
| 2011/0150814 A1 | 6/2011 | Woo et al. |
| 2011/0152146 A1* | 6/2011 | Denutte ............... A61K 8/11 510/119 |
| 2011/0268778 A1 | 11/2011 | Dihora et al. |
| 2011/0268802 A1 | 11/2011 | Dihora et al. |
| 2011/0269657 A1 | 11/2011 | Dihora et al. |
| 2011/0269658 A1 | 11/2011 | Dihora et al. |
| 2012/0276210 A1 | 11/2012 | Dihora et al. |
| 2013/0090390 A1* | 4/2013 | Singer ................. A61Q 13/00 514/772 |
| 2014/0037703 A1 | 2/2014 | Dihora et al. |
| 2014/0079747 A1 | 3/2014 | Dihora et al. |
| 2014/0086965 A1 | 3/2014 | Dihora et al. |

FOREIGN PATENT DOCUMENTS

| | | |
|---|---|---|
| WO | WO 9826808 | 6/1998 |
| WO | WO-03-015736 A2 | 2/2003 |
| WO | WO-2008-104690 A1 | 9/2008 |

OTHER PUBLICATIONS 10-undecenal, SCIFINDER Database [online], American Chemical Society, 2016 [retrieved on Feb. 15, 2016], Retrieved from the Internet: <URL:https://scifinder.cas.org>, p. 1.*
U.S. Appl. No. 14/032,888, filed Sep. 20, 2013, Jianjun Justin Li et al.
U.S. Appl. No. 14/045,670, filed Oct. 3, 2013, Dihora et al.
PCT International Search Report, PCT/US2014/042892, mailed Sep. 29, 2014, 9 pages.

* cited by examiner

*Primary Examiner* — Michael B Pallay
(74) *Attorney, Agent, or Firm* — George H. Leal; Andrew J. Mueller

(57) ABSTRACT

Absorbent articles comprising one or more complexed or encapsulated compounds compounds selected from: melonal, adoxal, trans-2-hexenal, ligustral, Floral Super, Florhydral, 5-methyl-2-thiophene-carboxaldehyde, hydratropic aldehyde, undecenal, 9-undecenal, 10-undecenal, trans-4-decenal, cis-6-nonenal, isocyclocitral, precyclemone b, (E)-2,(z)-6-nonadienal, undecyl aldehyde, methyl-octyl-acetaldehyde, Lauric aldehyde, silvial, vanillin, floralozone; are particularly effective in reducing malodors coming from degradation of proteinaceous materials such as food, menses or feces.

16 Claims, No Drawings

ABSORBENT ARTICLE COMPRISING COMPLEXED OR ENCAPSULATED REACTIVE COMPOUNDS

FIELD OF THE INVENTION

The present invention relates to an absorbent article comprising a one or more complexed or encapsulated compounds which are particularly effective in counteracting malodors.

BACKGROUND OF THE INVENTION

Absorbent articles according to the present invention are articles which can be used to absorb any type of fluid. These articles include absorbent articles for personal hygiene (like for example sanitary napkins, pantyliners, tampons, inter labial articles, adult incontinence articles such as adult incontinence pads and diapers, baby diapers, breast pads and hemorrhoid pads). Other absorbent articles according to the present invention can be for example absorbent paper towels, wipes, toilet paper, or facial tissues. Such articles are commonly used to absorb and in some cases retain bodily fluids and other exudates excreted by the human body, such as urine, menses, fecal materials or mucus. Paper towels, wipes, facial tissues and toilet paper may be used also to absorb kitchen and food residues and/or any kind of dirt or waste. In many cases the absorbed materials, can be malodourant or can generate malodors with time while the article is still being used or after it has been thrown in the trash. Therefore, methods and materials for controlling and reducing malodors in absorbent articles have been developed. Fragrance materials have been widely used for this purpose, as well as ingredients such as silica or zeolites which are able to entrap some of the malodor generating molecules. The use of fragrance materials, however, tends to provide an overwhelming perfume scent to the product before use which may be undesirable in certain cases. The use of compounds capable of chemically reacting with the malodorous molecules and/or to interacting with nose receptors has also been described. However many of these compounds are very volatile or highly reactive so that it is difficult to preserve them within the article until the time the compound is needed for use, moreover the reactivity and the efficacy of these compounds varies significantly from one compound to the other and it is different when the source of malodor is different.

Some of these compounds have been also described as being incorporated into the absorbent articles as encapsulated materials (e.g. starch encapsulation) or as complexes with other molecules which, by way of complexation, reduce their volatility and protect their reactive sites. A typical example is the use of cyclodextrin complexes.

It is in general desired that the complexed or encapsulated compound is released upon wetting or use of the article, capsules are in general dissolved by wetting or broken by mechanical action thus releasing the compound. Wetting in general allows the complexed compounds to be released by the complexing molecule such as cyclodextrin. However only a limited number of compounds have been described which possess all the necessary properties so that they can at the same time form stable encapsulates or complexes in an effective manner and also be completely released when desired.

In addition, the known reactive compounds are often effective in reacting with malodourant molecules containing Nitrogen atoms (amine type odors, typically deriving from the degradation of urine) but less effective in reacting with malodourant molecules containing Sulphur atoms (thiol type malodors, typically associated with menstrual fluids and protein degradation).

There thus still remains a desire to provide new improved malodor control compositions for incorporation into absorbent articles. The improved malodor control compositions of the present invention contain new reactive compounds. These new reactive compounds form capsules/complexes in a complete fashion which are sufficiently stable upon storage when introduced into the absorbent articles, the reactive compounds are effectively released from the capsules/complex upon the occurrence of the desired trigger action (e.g. wetting or mechanical friction) and are able to neutralize malodors more effectively with respect to known compounds, including neutralizing a larger number of malodourant substances.

Encapsulation/complexation also beneficially prevents hydrophobic reactive compounds according to the present invention from negatively impacting absorbency or impacting the properties of adhesives or glues which might be present in the absorbent article e.g glues keeping several layers of the article together or, in the case of sanitary napkins and pantyliners, the panty fastening adhesive.

In addition to the advantages mentioned above the identification of new reactive compounds for use as encapsulated or complexed materials in absorbent articles will allow the formulators to have a broader palette of materials to choose from. Most of the known and new reactive compounds usable herein have an individual odor character once they are released from the complex, so that the addition of new ingredients to the palette from which a formulator can choose from allows them to develop more different and personalized perfume notes and accords.

SUMMARY OF THE INVENTION

The present invention relates to absorbent articles comprising one or more complexed or encapsulated compounds selected from: melonal, adoxal, trans-2-hexenal, ligustral, Floral Super, Florhydral, 5-methyl-2-thiophene-carboxaldehyde, hydratropic aldehyde, undecenal, 9-undecenal, 10-undecenal, trans-4-decenal, cis-6-nonenal, isocyclocitral, precyclemone b, (E)-2-(z)-6-nonadienal, undecyl aldehyde, methyl-octyl-acetaldehyde, Lauric aldehyde, silvial, vanillin, floralozone.

The absorbent articles of the present invention in case no other free perfumes are present can exhibit no, or very little, scent prior to use and still be very effective in counteracting malodours. During use of the articles, fluids contact the capsule or complex and/or a mechanical action ruptures the capsule membrane and provides an effective release of the complexed or encapsulated components. The absorbent articles of the present invention are effective in reducing malodors originating from food and body fluids degradation, and particularly effective in reducing malodors originating from the degradation of proteinaceous material, which are typically found in menstrual fluid, feces, food residues, mucus, body fluids etc.

The present invention can provide sustained odor control for the period of time the absorbent article is typically used by a consumer, this is particularly relevant for absorbent hygienic articles which can be worn typically about 4 hours during the daytime and typically about 8 hours overnight.

The present invention further relates to a method of reducing the malodor associated with the degradation of food and body fluids such as urine, menses, and/or feces, comprising the step of contacting the malodourant material with an absorbent article of the present invention.

The present invention also relates to a method of making an absorbent article according to the present invention.

DETAILED DESCRIPTION OF THE INVENTION

"Absorbent article" refers to articles that absorb any type of fluid. These articles are typically disposable and include paper towels, wipes, toilet paper, facial tissue, and absorbent hygienic articles. "absorbent hygienic articles" refers to devices that absorb and contain body exudates, such as urine, menses, blood and feces. The term "disposable" is used herein to describe absorbent articles which are not intended to be laundered or otherwise restored or reused as an absorbent article after a single use. Examples of absorbent hygienic articles include diapers, toddler training pants, adult incontinence pads or diapers, and feminine hygiene garments such as sanitary napkins, pantiliners, tampons, interlabial devices, breast pads, hemorrhoid pads, and the like.

Absorbent hygienic articles and components thereof, including the topsheet, backsheet, absorbent core, and any individual layers of these components, can have a body-facing surface and a garment-facing surface. As used herein, "body-facing surface" means that surface of the article or component which is intended to be worn toward or adjacent to the body of the wearer, while the "garment-facing surface" is on the opposite side and is intended to be worn toward or placed adjacent to the wearer's undergarments when the disposable absorbent article is worn.

Most absorbent hygienic articles of the present invention (except those for internal use such as tampons) typically comprise a topsheet, a backsheet, and an absorbent core disposed between the topsheet and backsheet.

The topsheet of the absorbent hygienic article is preferably compliant, soft feeling, and non-irritating to the wearers skin and hair. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers), polymeric materials such as apertured formed thermoplastic films, apertured plastic films, and hydroformed thermoplastic films, porous foams, reticulated foams, reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

The backsheet can be impervious to liquids (e.g., menses and/or urine) and can be preferably manufactured from a thin plastic film, although other flexible materials may also be used such as nonwovens. As used herein, the term "flexible" refers to materials which are compliant and will readily conform to the general shape and contours of the human body. The backsheet can prevent the exudates absorbed and contained in the absorbent core from wetting articles which contact the absorbent article such as bedsheets, pants, pajamas and undergarments. The backsheet can also be vapor permeable ("breathable"), while remaining fluid impermeable. The backsheet may comprise a woven or nonwoven material, polymeric films such as thermoplastic films of polyethylene or polypropylene, or composite materials such as a film-coated nonwoven material.

The backsheet can comprise panty fastening means applied on its surface, particularly the surface facing outside the absorbent article in order to allow the article to stay in place when worn between the user's crotch and panties. Such panty fastening means can be for example a layer of adhesive or mechanical means such as Velcro® or combination thereof. When an adhesive is present, typically a release paper is also present in order to protect the adhesive before use.

The backsheet and the topsheet can be positioned respectively adjacent the garment surface and the body surface of the absorbent core. The absorbent core can be joined with the topsheet, the backsheet, or both in any manner as is known by attachment means such as those well known in the art. Embodiments of the present invention are envisioned wherein portions of the entire absorbent core are unattached to either the topsheet, the backsheet, or both.

The absorbent core can be formed from any of the materials well known to those of ordinary skill in the art. Examples of such materials include multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers. Other suitable absorbent core materials include absorbent foams such as polyurethane foams or high internal phase emulsion ("HIPE") foams. Suitable HIPE foams are disclosed in U.S. Pat. Nos. 5,550,167, 5,387,207, 5,352,711, and 5,331,015.

For some absorbent articles, the absorbent core can be relatively thin, less than about 5 mm in thickness, or less than about 3 mm, or less than about 1 mm in thickness. Thickness can be determined by measuring the thickness at the midpoint along the longitudinal centerline of the pad by any means known in the art while under a uniform pressure of 1.72 kPa.

The absorbent core can comprise superabsorbent materials such as absorbent gelling materials (AGM), including AGM fibers, as is known in the art. The absorbent core can therefore constitute a layer comprising superabsorbent material.

The absorbent article can comprise other additional components, for example between the topsheet and absorbent core, such as a secondary topsheet or acquisition layer. The secondary topsheet or acquisition layer can comprise a tissue layer or a nonwoven, such as carded resin-bonded nonwovens, embossed carded resin-bonded nonwovens, high-loft carded resin-bonded nonwovens, carded through-air-bonded nonwovens, carded thermo-bonded nonwovens, spunbonded nonwovens, and the like. A variety of fibers can be used in the secondary topsheet or acquisition layer, including natural fibers, e.g. wood pulp, cotton, wool, and the like, as well as biodegradable fibers, such as polylactic acid fibers, and synthetic fibers such as polyolefins (e.g., polyethylene and polypropylene), polyesters, polyamides, synthetic cellulosics (e.g., RAYON®, Lyocell), cellulose acetate, bicomponent fibers, and blends thereof. The basis weight of the secondary topsheet or acquisition layer can vary depending upon the desired application.

The absorbent article can comprise further components such as side cuffs, typically found in diapers, or side wings or side flaps, typically found in sanitary napkins.

Absorbent catamenial tampons are absorbent articles for internal use in the vagina which are typically made by a pledget comprising absorbent fibers compressed to a cylindrical shape. Tampons can be "digital tampons" when they have a self sustaining shape and can be inserted with a finger or "applicator tampons" i.e. tampons which are introduced using an applicator. Tampons can also comprise an extraction cord so to facilitate extraction from the vagina.

The absorbent hygienic articles herein are preferably disposable after a single use.

Absorbent hygienic articles herein are often commercialized in packages containing a plurality of units, often the package is a plastic film or a carton box. Single units contained within the commercial package can be individually packaged or not.

The complexed or encapsulated compound of the present invention can be disposed in various locations in the absorbent article. In the case of paper towels, wipes, toilet paper and facial tissues the compound can be applied on any surface of any of the layers making up the article or be mixed with the cellulose fibers during the making process.

In the case of absorbent hygienic articles the complexed or encapsulated compound can be disposed on the garment-facing side or the body-facing side of the topsheet or absorbent core, or on the body-facing side of the backsheet. Preferably, the complexed or encapsulated compound is disposed on the absorbent core, and preferably on the body-facing side of the absorbent core. The complexed or encapsulated compound can also be disposed on other components of the absorbent article, when present, such as the garment-facing side or body-facing side of a secondary topsheet or acquisition layer.

In certain embodiments the complexed or encapsulated compound of the present invention is disposed in the absorbent article in a layer that is closer to the body-facing surface of the absorbent article than the absorbent core or a layer comprising superabsorbent material (e.g. absorbent gelling material ("AGM")). In some cases in order for the complexed or encapsulated compound to effectively release the compound it needs to come in contact with moisture. A problem exists when incorporating a complexed or encapsulated compound in an absorbent hygienic article, because other components, such as the absorbent core and/or superabsorbent material, of the absorbent article have a strong affinity for bodily fluids, including the moisture contained therein. When an absorbent article is insulted with bodily fluid, such as menses or urine, the complexed or encapsulated compound is thus in competition with the absorbent core and/or superabsorbent material for the moisture contained in the bodily fluid. The absorbent core and/or superabsorbent material has a strong affinity for the moisture and once the absorbent core and/or superabsorbent material contacts the bodily fluid, the absorbent core and/or superabsorbent material effectively "lock-up" the moisture of the bodily fluid, thereby reducing the amount of moisture available to contact the complexed or encapsulated compound and release the compound to provide odor control benefits. In these cases disposing the complexed or encapsulated compound in the absorbent article in a layer that is closer to the body-facing surface of the absorbent article than the absorbent core and/or a layer comprising superabsorbent material enables the complexed or encapsulated compound to come in contact with the bodily fluid preferentially before the bodily fluid comes into contact with the absorbent core and/or superabsorbent material. This results in more effective release of the compound and provides improved odor control benefits.

In the case of catamenial tampons the complexed or encapsulated compound can be present in any component of the tampon, including the absorbent compressed pledget forming the tampon body, the overwrap, and the extraction cord. For example it can be comprised in the tampon body, or on the tampon surface or, if an overwrap is present, on either surface of the overwrap. In case a secondary mass of absorbent material is present along the extension cord proximal to the extraction end of the tampon, the complexed or encapsulated compound can be comprised within this secondary mass.

Encapsulating Compounds

The reactive compounds of the present invention can be encapsulated using any technique known in the art. The term "Encapsulation" within the present invention is intended to encompass any technology which allows introducing a reactive compound according to the invention into an absorbent article as a solid in a mixture with other materials which are called in general "encapsulating materials". The reactive compounds when encapsulated are prevented from contacting other materials so to avoid unwanted reactions. Moreover, when encapsulated, their evaporation is prevented. Many types of capsules are known in the art and are used for the delivery of perfume ingredients. All these types of capsules are usable in the present invention. Capsules can have any size, typically used in the art and suitable herein are nanocapsules, microcapsules, and larger capsules. In general capsules will have a size such that their shorter diameter will be lower than 3 mm or lower than 1 mm.

Capsules allow the encapsulated composition to release when it is needed. Typically in the case of absorbent articles this corresponds to two cases:

1—when the article receives a liquid insult (e.g. when in absorbent hygienic articles menses or urine are discharged): in this case capsules comprise water soluble materials or materials which trigger release of the encapsulated compound when contacted with water or a water containing liquid.

2—when pressure or force is exerted on the article (e.g. in the case of paper towels and wipes, or in the case when an absorbent hygienic article is worn during a period of high activity): in this case, for example, breakable capsules having a shell of rupturable polymeric film can be used.

All these types of capsule are known in the art e.g. as perfume delivery systems.

These two cases should however be intended as non limiting examples. In fact any other trigger (or combination of triggers) can be used to release the encapsulated compound from the capsule, e.g. evaporation, diffusion, temperature, humidity, light etc. The release of the encapsulated compound can be instantaneous or sustained over time, depending on needs. The skilled person, based on the desired trigger action and release type, will be able to select the appropriate encapsulating material from those known in the art.

Capsules can use different encapsulating materials:

I. Polymers. Polymeric Materials can be Used as Encapsulating Materials.

Classical coacervates, water soluble or partly soluble to insoluble charged or neutral polymers, liquid crystals, hot melts, hydrogels, perfumed plastics, microcapsules, nano- and micro-latexes, polymeric film formers, and polymeric absorbents, polymeric adsorbents, etc. are some examples. Polymeric capsules include but are not limited to:

a.) Matrix Systems: The compound to be encapsulated is dissolved or dispersed in a polymer matrix or particle. Such compounds, for example, may be dispersed into the polymer prior to formulating into the product. Diffusion of the encapsulated compound from the polymer is a common trigger that allows or increases the rate of compound release from a polymeric matrix system that is deposited or applied to the desired surface, although many other triggers are know that may control compound release. Absorption and/or adsorption into or onto polymeric particles, films, solutions, and the like are aspects of this technology. Nano- or micro-particles composed of organic materials (e.g., latexes) are examples. Suitable particles which can be used herein include a wide range of materials including, but not limited to polyacetal, polyacrylate, polyacrylic, polyacrylonitrile, polyamide, polyaryletherketone, polybutadiene, polybutylene, polybutylene terephthalate, polychloroprene, poly ethylene, polyethylene terephthalate, polycyclohexylene dimethylene terephthalate, polycarbonate, polychloroprene, polyhydroxyalkanoate, polyketone, polyester, polyethylene, polyetherimide, polyethersulfone, polyethylenechlorinates, polyimide, polyisoprene, polylactic acid, polymethylpentene, polyphenylene oxide, polyphenylene sulfide, polyphthalamide, polypropylene, polystyrene, polysulfone, polyvinyl acetate, polyvinyl chloride, as well as polymers or copolymers based on acrylonitrile-butadiene, cellulose acetate, ethylene-vinyl acetate, ethylene vinyl alcohol, styrene-butadiene, vinyl acetate-ethylene, and mixtures thereof.

"Standard" systems refer to those that are "pre-loaded" with the intent of keeping the pre-loaded compound associated with the polymer until the moment or moments of release. Such polymers may also suppress the neat product odor and provide a bloom and/or longevity benefit depending on the rate of compound release. One challenge with such systems is to achieve the ideal balance between 1) in-product stability (keeping the compound inside carrier until you need it) and 2) timely release (during use. Suitable micro-particles and micro-latexes as well as methods of making same may be found in USPA 2005/0003980 A1. Matrix systems also include hot melt adhesives and perfumed plastics. Polymer Assisted Delivery (PAD) matrix systems may include those described in the following references: US Patent Applications 2004/0110648 A1; 2004/0092414 A1; 2004/0091445 A1 and 2004/0087476 A1; and U.S. Pat. Nos. 6,531,444; 6,024,943; 6,042,792; 6,051,540; 4,540,721 and 4,973,422.

Silicones are also examples of polymers that may be used as encapsulating materials and can provide compound release benefits. Suitable silicones as well as making same may be found in WO 2005/102261; USPA 20050124530A1: USPA 20050143282A1; and WO 2003/015736. Functionalized silicones may also be used as described in USPA 2006/003913 A1. Examples of silicones include polydimethylsiloxane and polyalkyldimethylsiloxanes.

b.) Reservoir Systems: Reservoir systems are also known as a core-shell type technology, in which the compound to be released is surrounded by a release controlling membrane, which serves as a protective shell. The material inside the capsule is referred to as the core, internal phase, or fill, whereas the wall is sometimes called a shell, coating, or membrane. Depending on the type of shell materials the capsules can be activated by different mechanisms, for example the coating can be soluble in water or soluble in water solutions having a certain pH. In certain embodiments of the present invention the reservoir capsules have water insoluble shells and the core of the capsule is released upon mechanical activation.

Pressure sensitive capsules or friable capsules are examples of this technology. Friable capsules can be made in any sizes, and shapes, typically used are friable microcapsules. Any type of polymeric material can be used to make the shell of friable capsules, as well as any material can be used as a core material as known in the art. A skilled person will be able to determine which materials can be used to encapsulate certain core materials based on the knowledge available in the art concerning the compatibility of the materials (e.g. in general the shell material is selected so that core material will not act as a solvent on it). Friable microcapsules will be described now in more detail, it is clear to the skilled person that the same type of materials and construction can be used to make larger or smaller capsules.

Friable microcapsules are capsules where the outer shell is made from any polymer or mixture of polymers. Typical polymers which can be used to be comprised in the shell of a friable microcapsule include melamine-formaldehyde or urea-formaldehyde condensates, melamine-resorcinol or urea-resorcinol condensates, nylon, polyacrylates, polyethylenes, polyamides, polyamides, polystyrenes, polyisoprenes, polycarbonates, polyesters, polyureas, polyurethanes, polyolefins, polysaccharides, epoxy resins, vinyl polymers, silk, wool, gelatin, cellulose, proteins and mixture thereof as well as co-polymers comprising, as co monomers, monomers contained in these mentioned polymers.

Among the most stable friable microcapsules are those comprising polyoxymethyleneurea (PMU)-based polymers, melamine-formaldehyde based polymers, and polyacrylate based polymers.

In some embodiments the microcapsule outer shell material can include a polyacyrylate material. Any polymer or copolymer including acrylate or metacrylate monomers can be used in the present invention, preferred materials are those known in the art as forming polyacrylate microcapsules such as, for example, those described in US2012-276210A1. In some embodiments the shell of the microcapsules comprises a polyacrylate copolymer, in some case can be a polyacrylate random copolymer.

A friable microcapsule is configured to release its core substance when its outer shell is ruptured. The rupture can be caused by forces applied to the outer shell during mechanical interactions. Friable microcapsules can have various fracture strengths. Each microcapsule can have an outer shell with a fracture strength of 0.2-10.0 mega Pascals, when measured according to the Fracture Strength Test Method, described in co-pending application U.S. 61/703, 587. As an example, a microcapsule can have an outer shell with a fracture strength of 0.2-2.0 mega Pascals.

Friable microcapsules can have various core to outer shell ratios. Each microcapsule has an outer shell, and a core within the outer shell, and a core to outer shell ratio (in weight) from 99-1 to 1-99, or from 95-5 to 10-90, or from 50-50 to 90-10.

Friable microcapsules can have various outer shell thicknesses. In some embodiments the microcapsule can have an outer shell with an overall thickness of 1-300 nanometers or 2-200 nanometers.

For application to an anhydrous product such as an absorbent article, it is especially preferred that the microcapsule is applied as an anhydrous particle. Such particles may be produced by spray drying as describe in patent application US61/703,616. In the instances where friable microcapsules are spray dried, it is preferable to apply these particles in a paste or slurry comprising a carrier vehicle.

These particles may also be directly applied to the substrate as a powder without using a carrier vehicle. It is for example possible to apply the spray dried particles to an adhesive that is part of a peelable surface containing an adhesive. Examples of peelable surfaces containing adhesives may include for example the panty fastening backsheet adhesive or the wings adhesive, such that when a consumer peels back the surface, a burst of fragrance is delivered to consumers and the fragrance can then be transferred to the clothing for added odor protection.

Alternately, the friable microcapsules can be delivered via an aqueous slurry to surfaces of the absorbent article and allowed to dry.

Friable microcapsules and relative methods for making them as well as methods to measure their properties which can be used herein are described in co-pending applications U.S. 61/703,616 and U.S. 61/703,587. which are incorporated herein by reference.

Example methods for making polyacrylate microcapsules are disclosed in U.S. Patent Application Ser. Nos.61/328,949; 61/328,954; 61/328,962; and 61/328,967. which are incorporated herein by reference.

II. Starches: The use of a starch encapsulation technology allows one to modify the properties of the compound to be encapsulated, for example, by converting a liquid compound into a solid by adding ingredients such as starch. The benefit includes increased retention for volatile compounds during product storage. Upon exposure to moisture, a release may be triggered. Another benefit is that the starch encapsulation allows the product formulator to select compounds or concentration of compounds that normally cannot be used without the presence of starch encapsulation. Suitable starch encapsulation examples as well as methods of making the same may be found in US 2005/0003980 A1 and U.S. Pat. No. 6,458,754 B1.

In one aspect, starch encapsulated compounds may be made by preparing a mixture comprising starch, water, acid and the compound(s) which need to be encapsulated, the acid being incorporated in the mixture in an amount sufficient to lower the pH of the starch-water mixture by at least 0.25 units; and spray drying the mixture thereby forming the encapsulated compound(s). In the first step in the process of compound(s) encapsulation, an aqueous mixture is prepared comprising starch, water, the compound(s) which need to be encapsulated and acid. These ingredients may be added in any order, but usually the starch-water mixture is prepared first and subsequently, either sequentially or together, the acid and compound(s) to encapsulate are added. When they are added sequentially, the acid may be added prior to the ingredient for encapsulation. Alternatively, the acid is added after the ingredient for encapsulation. The concentration of starch in the aqueous mixture may be from as low as 5 or 10 wt % to as high as 60 or even 75 wt %. Generally the concentration of starch in the mixture is from 20 to 50 wt %, more usually around 25 to 40 wt % in the aqueous mixture.

Suitable starches can be made from raw starch, pregelatinized starch, modified starch derived from tubers, legumes, cereal and grains for example corn starch, wheat starch, rice starch, waxy corn starch, oat starch, cassava starch, waxy barley starch, waxy rice starch, sweet rice starch, amioca, potato starch, tapioca starch and mixtures thereof. Modified starches may be particularly suitable for use in the present invention, and these include hydrolyzed starch, acid thinned starch, starch having hydrophobic groups, such as starch esters of long chain hydrocarbons ($C_5$ or greater), starch acetates, starch octenyl succinate and mixtures thereof. In one aspect, starch esters, such as starch octenyl succinates are employed.

The term "hydrolyzed starch" refers to oligosaccharide-type materials that are typically obtained by acid and/or enzymatic hydrolysis of starches, preferably corn starch. It may be preferred to include in the starch water-mixture, a starch ester. Particularly preferred are the modified starches comprising a starch derivative containing a hydrophobic group or both a hydrophobic and a hydrophilic group which has been degraded by at least one enzyme capable of cleaving the 1,4 linkages of the starch molecule from the non-reducing ends to produce short chained saccharides to provide high oxidation resistance while maintaining substantially high molecular weight portions of the starch base. The aqueous starch mixture may also include a plasticizer for the starch. Suitable examples include monosaccharides, disaccharides, oligosaccharides and maltodextrins, such as glucose, sucrose, sorbitol, gum arabic, guar gums and maltodextrin.

The acid used in the process of the invention may be any acid. Examples include sulfuric acid, nitric acid, hydrochloric acid, sulfamic acid and phosphonic acid. In one aspect, carboxylic organic acids are employed. In another aspect, organic acids comprising more than one carboxylic acid groups are employed. Examples of suitable organic acids include citric acid, tartaric acid, maleic acid, malic acid, succinic acid, sebacic acid, adipic acid, itaconic acid, acetic acid and ascorbic acid, etc. In one aspect, saturated acids, such as citric acid, are employed.

Following the formation of the aqueous mixture comprising starch, water, perfumes and acid, the mixture is mixed under high shear to form an emulsion or dispersion of ingredient for encapsulation in the aqueous starch solution.

Any suitable technique may then be used for the final stage of processing where the aqueous mixture including acid and perfumes is atomized and dried. Suitable techniques include, but are not limited to those known in the art including spray drying, extrusion, spray chilling/crystallization methods, fluid bed coating and the use of phase transfer catalysts to promote interfacial polymerization. Spray efficiencies may be increased by methods known in the art, such as by using high drying towers, lightly oiling the chamber walls, or using preconditioned air in which the moisture has been substantially removed.

Coated Capsules

In some embodiments the primary materials forming the capsule as described so far, may be further encapsulated with a secondary coating material. Any of the capsule types mentioned so far can be used in the present invention as such or with an additional secondary coating material.

An additional secondary coating material can help in reducing the scent perception, in reducing evaporation of volatile components over time (especially at elevated temperatures and humidity conditions) and in increasing chemical stability of the complexed compound by reducing the exposure of the complexed compounds (which in the present invention comprise highly reactive materials) to prematurely react or decompose so they are no longer functional or have a different odor character when activated. Additionally the use of coated capsules can allow altering the release characteristic of the encapsulated material (slowing or accelerating its release, or changing the release trigger, for example introducing a pH trigger). Generally, any second material that is added to or applied directly to a primary encapsulating material that accomplishes one or more of the above functions is characterized as a coating. The secondary coating may be directly applied using a second process step following creation of the primary capsule, using a process such as prilling, or using any fluidized bed process to apply a secondary surface coating (for example a Wurster Coater).

Coating compositions which are suitable for the present invention are all capsule coating compositions which are commonly known in the art. These include for example: polysaccharides (for example, but not limited to unmodified starch, chemically modified starch, dextrins, cyclodextrin and cyclodextrin derivatives), natural and artificial/synthetic waxes, esters and ester derivatives, fatty acids, natural and synthetic and chemically modified lipids, fatty alcohols, hydrocarbons (liner or branched, petrolatum), enteric coating compositions (such as the Eudragit series of Methacrylic acid co-polymers), polyvinyl alcohols, polyethylene glycols, silicones (for example, but not limited to silicone copolymers and functionalized silicones), surfactants, emulsifiers, polypropylene glycols, cellulose derivatives (methyl cellulose, hydroxypropyl cellulose), glycerin, mono and diglycerides, polyglycerol and polyglycerol esters and emulsifiers employed in food applications.

An example of the preparation of a coated capsule which can be used in the present invention has been described in U.S. Pat. No. 4,973,422 (see in particular Example 2).

Complexed Compounds

For "complex" it is intended an "inclusion complex" within the meaning of IUPAC Compendium of Chemical Terminology 2nd Edition (1997) wherein the complexing agent is the host and the complexed compound is the "guest". Examples of complexing agents are cyclodextrins. As used herein, the term "cyclodextrin" includes any of the known cyclodextrins such as substituted and unsubstituted cyclodextrins containing from about six to about twelve glucose units, for example alpha-cyclodextrin, beta-cyclodextrin, gamma-cyclodextrin and/or their derivatives and/or mixtures thereof. For example, the cyclodextrin complex of the present invention can comprise cyclodextrin selected from the group consisting of beta-cyclodextrin, alpha-cyclodextrin, hydroxypropyl alpha-cyclodextrin, hydroxypropyl beta-cyclodextrin, methylated-alpha-cyclodextrin, methylated-beta-cyclodextrin, and mixtures thereof. Cyclodextrin complexes of compounds which are active against malodors can be prepared as known in the art for example using the kneading method described in U.S. Pat. Nos. 5,571,782 and 5,543,157 or, preferably, using the spray drying method described in WO2008/104690A2.

Thiol Vapour Pressure Suppression Index

The reactivity against malodors of the complexed or encapsulated compounds according to the present invention is measures using the "thiol vapor pressure suppression index" (TVPS). of more than 20. Complexed or encapsulated compounds according to the present invention have been found to have a TVPS higher than 20.

Thiol Vapor Pressure Suppression (TVPS) index is a measure of the reduction in butanethiol concentration in the headspace by a compound, as measured using a fast GC instrument, the zNose 7100 (Electronic Sensor Technologies, Newbury Park, Calif.). Before any measurements the instrument is calibrated according to manufacturer's instructions under the same experimental settings. The instrument has a DB-5 column (EST Part No. SYS7100C5, Electronic Sensor Technologies, Newbury Park, Calif.) 1 m in length, 0.25 µm phase thickness, and 0.25 mm in diameter. The experimental settings for TVPS measurements are:

Sampling time: 10 s
Sensor Temperature: 40° C.
Initial Column Temperature: 40° C.
Inlet Temperature: 40° C.
Valve Temperature: 40° C.
Column Temperature Ramp Rate: 10 C.°/s
Final Column Temperature: 200° C.

TVPS of a compound is measured in the following way: 100 µl±1 µl of a 1% v/v butanethiol (99%, purity) solution in ethanol (200 proof) is added into a 1 ml vial (8×40 mm). These vials are borosilcate glass straight walled vial. A suitable butanethiol is item 112925 from Sigma-Aldrich (Sigma-Aldrich, St. Louis, Mo.). In another 1 ml vial (8×40 mm), 5 µl±0.2 µl of the compound is added. Both open vials are then placed inside a 20 ml headspace vial (22×75 mm), and the vial is immediately sealed using a screw thread closure with PTFE/Silicone septa. The vial is heated to 37° C. for 4 hours. After 4 hours, the vial is removed from the oven and let to equilibrate at 25° C.±2° C. for 15 minutes. The headspace inside the vial is sampled using the zNose following the experimental protocol outlined above. Samples with butanethiol alone, and the volatile active alone, are run using the same protocol to identify the peaks for both materials. An acceptable retention index for butanethiol is 720±30. If the peaks butanethiol peak and the volatile material peak co-elute, one skilled in the art can modify the protocol settings to separate those peaks. A minimum resolution of 1.5 should be obtained. For example one can change the column temperature ramp rate. In between samples, the instrument needs to be cleaned to remove any trace materials. To clean the instrument, the instrument is run without samples as needed until no peaks greater than 100 counts are observed.

The amount of butanethiol in the headspace is measured from the area of the peak on the chromatograph for butanethiol ($A_{BtSH,Rx}$). To calculate the percentage of butanethiol reduction in the headspace, a control with the butanethiol solution without the volatile material is run in the same manner and the area is measured as well ($A_{BtSH,C}$). TVPS is then measured as the percentage reduction in butanethiol area calculated using the following formula:

$$TVPS = \frac{A_{BtSH,C} - A_{BtSH,Rx}}{A_{BtSH,C}} \times 100$$

An example of the type of measurements obtained with the instrument is:

| Sample | Butanethiol Peak Retention Index | Area (counts) |
| --- | --- | --- |
| Butanethiol Control Vial 1: 100 µl of 1% v/v butanethiol in ethanol Vial 2: Empty | 720 | $A_{BtSH, C}$ = 4934 |
| Butanethiol + Florhydral Vial 1: 100 µl of 1% v/v butanethiol in ethanol Vial 2: 5 µl Florhydral | 720 | $A_{BtSH, Rx}$ = 2442 |

Example TVPS calculation for $$TVPS = \frac{4934 - 2442}{4934} \times 100 = 50.5\%$$

The value of TVPS for several compounds suitable for the invention is presented in the table below. TVPS for the compounds indicated with (*) have been approximated using a mathematical model calculated starting from real measurements on a large number of compounds. The model is created using the QSAR software CACHe ProjectLeader WorkSystem Pro 7.1. Using the molecular structure from the compounds for which TVPS was evaluated, several molecular properties are calculated. A regression algorithm is the used to calculate the best fit to predict TVPS based on the 4 molecular descriptors that best fit the data. The model is then used to predict TVPS for other compounds using the same software. The values of TVPS approximated with the molecular modeling system are presented for illustration only, for the avoidance of doubt it is specified that the TVPS values for use in the present inventions are only the TVPS values measured with the zNose analytical method described above.

|  | TVPS |
|---|---|
| melonal | 20.4 |
| adoxal | 24.4 |
| trans-2-hexenal | 27.1 |
| ligustral | 42.5 |
| Floral Super | 52.4 |
| Florhydral | 53.3 |
| 5-methyl-2-thiophene-carboxaldehyde | 67.4 |
| hydratropic aldehyde(*) | 72.0 |
| Undecenal(*) | 26.2 |
| 9-undecenal(*) | 67.5 |
| 10-undecenal(*) | 52.0 |
| trans-4-decenal(*) | 60.3 |
| cis-6-nonenal(*) | 57.1 |
| isocyclocitral(*) | 51.4 |
| precyclemone b(*) | 40.7 |
| (E)-2-(z)-6-nonadienal(*) | 35.8 |
| undecyl aldehyde(*) | 34.9 |
| methyl-octyl-acetaldehyde(*) | 30.2 |
| Lauric aldehyde(*) | 26.6 |
| silvial(*) | 25.8 |
| vanillin(*) | 23.7 |
| floralozone(*) | 23.5 |
| Hexylcinnamic aldehyde(**) | 8.0 |
| (**) neral | 17.1 |
| ethyl vanillin (**) | 2.9 |

Compound indicated as (**) indicate prior art compounds.

As it can be seen, some of the compounds mentioned in the prior art as being very effective in general for the control of malodors in absorbent articles, such as Hexylcinnamic aldehyde, have surprisingly low TVPS values. It is believed that such compounds, while very effective against some of the malodourant compounds typically found in absorbent articles, such as those comprising ammonia or amine groups, are surprisingly less effective in counteracting other types of malodors such as those deriving from protein degradation and containing thiol groups. Reactive compounds according to the present invention, having relatively high TVPS values are surprisingly effective in counteracting both types of malodourant molecules and are therefore overall more effective in neutralizing malodors in a broader range of situations.

The complexed or encapsulated reactive compounds of the present invention can be selected from the following list:
(a): melonal, adoxal, trans-2-hexenal, ligustral, Floral Super, Florhydral, 5-methyl-2-thiophene-carboxaldehyde, hydratropic aldehyde, undecenal, 9-undecenal, 10-undecenal, trans-4-decenal, cis-6-nonenal, isocyclocitral, precyclemone b, (E)-2,(z)-6-nonadienal, undecyl aldehyde, methyl-octyl-acetaldehyde, Lauric aldehyde, silvial, vanillin, floralozone.

All these compounds in list (a) are particularly reactive toward malodourant molecules containing Sulphur atoms (thiol type malodors, typically associated with protein degradation e.g. in menstrual fluids, feces, food etc). The primary function of the complexed or encapsulated reactive compounds is to chemically react with malodors, such as malodourant molecules containing Nitrogen atoms (amine type odors, typically deriving from the degradation of urine or certain foods like onions) and/or malodourant molecules containing Sulphur atoms (thiol type malodors, typically associated with protein degradation e.g. in menstrual fluids, feces, food etc). Ammonia/amines are one component of malodor associated with the absorption of bodily fluids, such as menses or urine. For example, ammonia/amines are typically present in high amounts in absorbent products used for urine absorption due to degradation of urea. Ammonia/amines and their derivatives can react with aldehydes and/or ketones to form imines (according to the so-called Schiff base reaction).

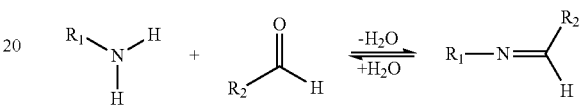

This reaction is catalyzed by enzymes and/or by a slightly acidic pH 4 to 5. The moderate acid requirement is necessary to allow protonation of the hydroxyl intermediate to allow water to leave.

Malodourant sulphur based compounds are typically generated by the degradation of proteins e.g. in menstrual fluids feces or food and so their control is particularly important in menstrual absorbent articles such as sanitary napkins or pantyliners as well as in other absorbent articles which get in contact with other proteinaceous materials such food residues or feces. The mechanism of action is not fully understood at the moment, but it is believed that it is connected to the fact that Thiols can react with aldehydes and ketones to form thioacetals and tioketals.

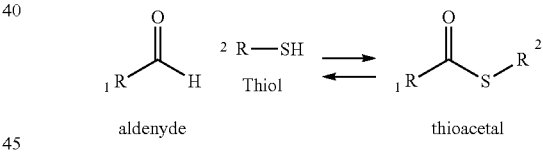

In principle the chemical reactions described above can be obtained from any aldehyde, but in practice the reactivity of aldehydes in these type of reactions and in the specific context of an absorbent article is very different. The reactive compounds of the present invention are effective in reacting with Nitrogen based malodourant molecules and particularly effective in reacting with sulphur based malodourant molecules.

The particularly high reactivity of the reactive compounds of the invention towards sulphur based malodourant molecules renders the present invention particularly effective for use in absorbent articles which are used to absorb menses.

In addition the reactive compounds of the present invention are particularly advantageous in the specific context of absorbent articles because they have a pleasant and low intensity odor and are also able to be complexed or encapsulated effectively and to be quickly released when needed.

Another important aspect of the present invention is that each complexed or encapsulated reactive compound has an individual character in terms of odor. Therefore their introduction within an absorbent article also represents the possibility to provide not only reactivity on malodors but also individual fragrant notes which can be combined with other odorous components (encapsulated/complexed and/or in free uncomplexed form) thus allowing the formulator to obtain a broader range of fragrances being released by the product when used i.e. when the encapsulated/complexed reactive compound is activated.

In the present invention, other selected additional compounds in complexed or encapsulated form can be optionally used in combination with the new reactive compounds, described above in list (a). Preferred additional compounds are listed here below in lists (b), (c), (d) and (e).

Suitable selected additional aldehydes and/or ketones include the following listed in list (b): hexyl cinnamic aldehyde, alpha-amylcinnamic aldehyde, p-anisaldehyde, benzaldehyde, cinnamic aldehyde, cuminic aldehyde, decanal, cyclamen aldehyde, p-t-butyl-alpha-methyldihydrocinnamaldehyde, 4-hydroxy-3-methoxycinnamaldehyde, vanillin isobutyrate, 2-phenyl-3-(2-furyl)prop-2-enal, ethyl vanillin acetate, vanillin acetate, heptanal, lauryl aldehyde, nonanal, octanal, phenylacetaldehyde, phenyl propyl aldehyde, salycil aldehyde, citral, 2,4-dihydroxy-3-methylbenzaldehyde, 2-hydroxy-4-methylbenzaldehyde, 5-methyl salicylic aldehydes, 4-nitrobenzaldehyde, o-nitrobenzaldehyde, 5-ethyl-2-thiophenecarbaldehyde, 2-thiophenecarbaldehyde, asaronaldehyde, 5-(hydroxymethyl)-2-furaldehyde, 2-benzofurancarboxaldehyde, 2,3,4-trimethoxybenzaldehyde, protocatechualdehyde, heliotropine, 4-ethoxy-3-methoxy benzaldehyde, 3,4,5-trimethoxybenzaldehyde, 3-hydroxybenzaldehyde, o-methoxycinnamaldehyde, 3,5-dimethoxy-4-hydroxycinnamaldehyde, 2,8-dithianon-4-3n-4-carboxaldehyde, sorbinaldehyde, 2,4-heptadienal, 2,4-decadienal, 2,4-nonadienal, 2,4-nonadienal, (E,E)-,2,4-octadien-1-al, 2,4-octadienal, 2,4-dodecadienal, 2,4-undecadienal, 2,4-tridecadien-1-al, 2-trans-4-cis-7-cis-tridecatrienal, piperonylidene propionaldehyde, 2-methyl-3-(2-furyl)acrolein, 2,4-pentadienal, 2-furfurylidene butyrraldehyde, helional, lyral, 3-hexenal, safranal, veratraldehyde, 3-(2-furyl)acrolein, pyruvaldehyde, ethanedial, 1-(2,6,6-trimethyl-1-cyclohexenyl)pent-1-en-3-one; 4-(2,6,6-trimethyl-1-cyclohexen-1-yl)-3-Buten-2-one; 4-(2,6,6-trimethyl-2-cyclohexen-1-yl)-3-buten-2-one, 5-(2,6,6-Trimethyl-2-cyclohexen-1-yl)-4-penten-3-one, (E)-4-(2,2-dimethyl-6-methylidenecyclohexyl)but-3-en-2-one.

Compounds in list (b) are additional aldehydes and/or ketones which are able to react with some classes of malodourant compounds and do not have unpleasant odor. One or more of these other selected aldehydes and/or ketones can be optionally used in complexed or encapsulated form in combination with those mentioned previously in list (a).

Other additional optional compounds can be present in complexed or encapsulated form.

These include in particular other fragrance/masking/reacting components. In some embodiments at least part of the additional components are selected from the following lists (c), (d) and (e).

Components from list (c) are menthol, menthyl acetate, menthyl lactate, menthyl propionate, menthyl butyrrate, menthone, mint terpenes, laevo-carvone, Cis-3-Hexenol & Cis-3-Hexenyl acetate, koavone, methyl dioxolan.

These are all compounds which primary function is to mask malodors. This may occur through vapor pressure suppression of the malodor or by overwhelming the unpleasant malodor with the pleasant odor of the fragrance component. These materials, when used, may significantly reduce the ability to detect the malodors. The masking ability to hide malodors is possible due to the volatile nature of the materials selected, which are released from the complex or capsule in the absorbent article and are then inhaled into the nose of a consumer, generally within somewhat close range of the absorbent article, e.g. within about 0 to 10 meters of the article by normal breathing (although this should in no way be intended to limit the scope of the invention).

Components from class (d) are methyl-dihydrojasmonate, methyl jasmonate, eucalyptol, tetrahydro-linalool, Phenyl-Ethyl alcohol, Hexyl iso-butyrate, Linalyl acetate, Benzyl acetate, Benzyl alcohol, or mixture thereof. These are volatile materials which are well complexed in particular when the complexing agent is a cyclodextrin and are release very quickly upon contact with a water based liquid. Their presence allows the absorbent article to respond more quickly to an insult of malodourant liquid by releasing a compound that have a good general masking effect against malodors, in particular, being very volatile, reduces the vapor pressure of other malodourant compounds slowing down their evaporation rate.

Other suitable malodor masking and fragrance components which can optionally be used in complexed or encapsulated form in combination with those of list (a) include those in the following list e):

e) camphor, p-menthane, limonene, cresol, linalool, myrcenol, tetra hydromyrcenol, di-hydromyrcenol, myrcene, citronellol, citronellyil derivatives, geraniol, geranyl derivatives, mugetanol, eugenol, jasmal, terpineol, pinanol, cedrene, damascone, beta pinene, cineole and its derivatives, nonadienol, ethylhexanal, octanol acetate, methyl furfural, terpinene, thujene, amylacetate, camphene, citronellal, hydroxycitronellal, ethyl maltol, methyl phenyl carbinyl acetate, dihydrocumarin, di-hydromyrcenyl acetate, geraniol, geranial, isoamylacetate, ethyl, and/or triethyl acetate, para-cresol, para-cymene, methyl abietate, hexyl-2-methyl butyrate, hexyl-2-methyl butyrate, and mixtures thereof.

All the compounds mentioned within the present application, unless a specific isomeric form is specified, also include their isomeric forms, diastereomers and enantiomers.

It may be that, for certain components, the same component can be considered both a malodor reactive component, a malodor masking component, and/or a fragrance component.

In embodiments of the invention wherein one or more compound of list a) is present in combination with one or more optional compounds of lists (b), (c), (d) or (e), the capsule or complex can be prepared mixing all compounds together before preparing the capsule or complex, or, alternatively, capsules or granules of complex containing only one or only some of the compounds can be prepared separately and then mixed according to the desires dosages before introduction into the absorbent article.

In some embodiments the absorbent articles of the present invention, in addition to the components from lists a), b), c), d) and e) in complexed or encapsulated form may also include components from the same lists or other fragrance components in free form (i.e. not complexed or encapsulated).

In the present invention it is however preferred that the absorbent article exhibits no noticeable scent (or very little scent) before use. As a result, it is preferred that no or a small level of other fragrant compounds are present and that the encapsulated/complexed compounds are complexed/encapsulated efficiently and completely so that only a low amount of free components are present before product usage and are released only during the utilization of the absorbent article.

In the case of cyclodextrin complexes, the percent of components that are complexed with cyclodextrin is greater than about 75%, greater than about 90%, or greater than about 95%. It should be understood that these levels of component complexation are directly associated with the complex formation process itself; i.e. the percentages do not represent a formulation design of adding a first percentage of components via a cyclodextrin complex and adding a second percentage of neat components.

Cyclodextrin complexes can be formed by various methods which are well known in the art. For example, U.S. Pat. Nos. 5,543,157, 5,571,782, and WO2008/104690A2 describe methods of forming cyclodextrin complexes.

As one example of a method of forming a cyclodextrin complex, a solvent (e.g., water or an organic solvent suitable for the organic compound to be complexed), unloaded cyclodextrin particles, and the organic compound which need to be complexed can be placed into a container and then mixed for a period of time to permit loading of organic molecules into "cavities" of cyclodextrin molecules. The mixture may or may not be processed further; e.g., processed through a colloid mill and/or homogenizer. The solvent is then substantially removed from the resulting mixture or slurry to yield cyclodextrin complex particles, e.g. via spray drying. Different manufacturing techniques may however impart different particle/complex characterizations, which may or may not be desirable in the absorbent articles, depending on the specific usage and conditions. In some embodiments the particles of cyclodextrin inclusion complexes have a low level of typically of less than about 20% by weight of the particles, or of less than about 10% by weight of the particles, or of less than about 6% by weight of the particles. Spray drying a slurry of inclusion complexes of cyclodextrin and organic compounds is one manufacturing technique capable of producing the cyclodextrin particles and cyclodextrin complexes having the above-noted, moisture levels. Cyclodextrin complexes can also be obtained using known techniques and an extrusion process (kneading) however the resulting material will in general contain a higher humidity and a lower complexation efficiency. Also US 2008/0213191 A1 from The Procter & Gamble Company provides a detailed overview of preferred techniques for preparing cyclodextrin complexes.

The one or more complexed or encapsulated compounds can be applied in a variety of ways, and in a variety of patterns, to the absorbent article. For example, when the capsules or complexes are dispersed in a carrier, the dispersion can be applied using conventional glue application equipment such as a slot applicator, which can be used for striped patterns, or air assisted applicators for patterned applications (like spray, spiral, serpentine, fibrils, Omega®, Signature® and the like) because this allows one to position the complexed or encapsulated compound in a way that it does not impact fluid acquisition (i.e. in a fem care article the material could not be applied in correspondence with the vaginal opening) and the pattern, having a large void space, allows fluid penetration also on the sides. Also patterned applications are helpful because they allow a precise application so that it is easier to avoid contact with the glue which connects the various layers of the absorbent article.

The one or more complexed or encapsulated compounds can be applied in powder form or can be incorporated into a liquid or semi-solid carrier and applied as a lotion. The one or more complexed or encapsulated compounds can be dispersed in a carrier to form a dispersion, and the dispersion applied to the absorbent article. The carrier can be selected from the group consisting of polysiloxane oil, mineral oil, petrolatum, polyethylene glycol, glycerin and the like, and mixtures thereof. The carrier is preferably polysiloxane oil, such as a silicone glycol copolymer (commercially available from Dow Corning as Dow Corning 190 Fluid).

The one or more complexed or encapsulated compounds are typically disposed in the absorbent article in an amount of from about 0.01 to about 1000 milligrams per absorbent article, in some embodiments from about 0.1 to about 100 milligrams per absorbent article, or from about 0.1 to about 500 milligrams per absorbent article.

The cited figures are applicable in general to any absorbent article, however absorbent articles can have very different sizes and therefore may contain more or less of the one or more complexed or encapsulated compounds, depending on need. The effectiveness of the odor control technology of the present invention is more effective than prior art odor control technologies for absorbent articles, therefore a lower level of perfume can be used to achieve effective odor control as shown in the table below. This provides an additional benefit of reducing contact dermatitis, skin irritation and is especially important for skin sensitive populations such as premature infants and incontinent adults (where skin barrier function may already be compromised from chronic hyperhydration and/or occlusion).

For example considering absorbent articles for personal hygiene the typical amounts are shown in the table below (weight indicated only refers to the one or more complexed or encapsulated compounds and not to the encapsulating/complexing materials):

TABLE 1

|  | Range | |
| --- | --- | --- |
| Absorbent article | Min | Max |
| Panty-Liners | 0.1 | 5 |
| Sanitary Napkins | 0.2 | 20 |
| Adult incontinence pads | 0.5 | 30 |
| Adult incontinence Diapers | 1 | 50 |
| Baby Diapers | 1 | 50 |

The present invention further encompasses a method of reducing malodor associated with bodily fluid such as urine, menses, and/or feces, comprising the step of contacting the bodily fluid with an absorbent article of the present invention. Preferably, the method reduces the malodor associated with menses, feces, food or other body fluids.

The present invention also encompasses a method of making an absorbent article which comprises the step of applying onto one of the materials making up the article one or more complexed or encapsulated compounds according to the present invention.

EXAMPLE 1

This is an example of an absorbent article of the present invention wherein the reactive compounds are complexed in cyclodextrin and are disposed on the garment-facing side of the secondary topsheet of the absorbent article.

The cyclodextrin complex is prepared as follows. The following components are added in order in a mildly agitated vessel, to create movement at the top of fluid, but without creating air bubbles: 55 grams of distilled water, 41 grams of beta cyclodextrin (contains nominally 12% moisture), and 4 grams of the Component Mixture of Table 1 below.

TABLE 2

COMPONENT MIXTURE

| INGREDIENT | AMOUNT (wt %) |
|---|---|
| Intreleven Aldehyde | 2 |
| Florhydral | 20 |
| Floral Super | 10 |
| Scentenal | 5 |
| Cymal | 25 |
| Floralozone | 10 |
| Adoxal | 1 |
| Methyl NonylAcetaldehyde | 1 |
| Melonal | 1 |
| o-anisaldehyde | 25 |

The resulting slurry is agitated for 30 minutes and then passed through a colloid mill (Gaulin mill). The rheology of the solution changes to a viscous slurry as the complexation occurs. The slurry is then dried via nozzle spray drying at an inlet temperature of approximately 195° C. and an outlet temperature of about 98° C. The resulting cyclodextrin complex is a powder having a moisture content of about 5%, by weight of the cyclodextrin complex, and a content of components complexed with cyclodextrin of about 8% to about 9%, by weight of the cyclodextrin complex. The cyclodextrin complex has less than about 2% of components that are uncomplexed with the cyclodextrin.

A LINES PETALO BLU CON ALI sanitary napkin, commercially available from Fater SpA, Italy, is obtained. The release paper wrapper of the sanitary napkin is removed and the sanitary napkin is unfolded into a flat, unfolded configuration. The sanitary napkin is then cut along one longitudinal side of the article (leaving the other longitudinal side intact). The topsheet is separated from the secondary topsheet ("STS"). On the garment-facing side of the STS, 20 milligrams of the cyclodextrin complex is applied in the center of the STS in an area of 3 cm×5 cm (a spatula is used to apply the cyclodextrin complex uniformly). The sanitary napkin is re-assembled in its original order and orientation, and a new thermal seal is provided along the cut longitudinal side.

EXAMPLE 2

This is an example of an absorbent article of the present invention wherein the cyclodextrin complex is formulated with a carrier and disposed on the garment-facing side of the secondary topsheet of the absorbent article.

A cyclodextrin complex is prepared as described in Example 1. 40 grams of the cyclodextrin complex are added slowly to 60 grams of a silicon glycol copolymer (Dow Corning 190 Fluid) in a mixer while stirring, obtaining a homogeneous dispersion which is kept under stirring.

A sanitary napkin, ALWAYS Ultra Regular available from The Procter & Gamble Company, is cut along a longitudinal side (leaving the other longitudinal side intact). The topsheet is separated from the secondary topsheet ("STS"). On the garment-facing side of the STS, 50 milligrams of the dispersion containing Dow Corning 190 Fluid and the cyclodextrin complex is applied in two thin spirals. The sanitary napkin is re-assembled in its original order and orientation, and a new thermal seal is provided along the cut longitudinal side.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising at least two complexed or encapsulated compounds selected from: 3-(3--propan-2-ylphenyl)butanal, 2methyl-3-[4-(2-methylpropyl)phenyl]propanal, (3-(4-ethylphenyl)-2,2-dimethylopropanal), trans-2-hexenal, Floral Super, 5-methyl-2-thiophene-carboxaldehyde, hydratropic aldehyde, undecenal, 9-undecenal, trans-4-decenal, cis-6-nonenal, isocyclocitral, precyclemone b, (E)-2,(z)-6-nonadienal, undecyl aldehyde, silvial, vanillin, and floralozone.

2. An absorbent article according to claim 1, wherein said one or more compounds are starch encapsulated.

3. An absorbent article according to claim 1, wherein said one or more compounds are encapsulated in reservoir type capsules and can be released by a mechanical action breaking the shell of the capsule.

4. An absorbent article according to claim 1, wherein said one or more compounds are encapsulated in a capsule having a secondary coating material.

5. An absorbent article according to claim 1, wherein the one or more compounds are comprised as cyclodextrin complexes.

6. An absorbent article according to claim 1, wherein said one or more compounds are comprised in at least two or three forms selected from (i) encapsulated in reservoir type capsules which can be released by a mechanical action breaking the shell of the capsule, (ii) cyclodextrin complexes, and (iii) starch capsules.

7. An absorbent article according to claim 1, the absorbent article being selected from paper towels, wipes, toilet paper, facial tissue, and absorbent hygienic articles.

8. An absorbent article according to claim 1, the absorbent article being an absorbent hygienic article selected from diapers, toddler training pants, adult incontinence pads or diapers, sanitary napkins, pantyliners, tampons, interlabial devices, hemorrhoid pads.

9. An absorbent article according to claim 1, further comprising one or more additional reactive compounds in complexed or encapsulated form selected from: hexyl cinnamic aldehyde, alpha-amylcinnamic aldehyde, p-anisaldehyde, benzaldehyde, cinnamic aldehyde, cuminic aldehyde, decanal, cyclamen aldehyde, p-t-butyl-alpha-methyldihydrocinnamaldehyde, 4-hydroxy-3-methoxycinnamaldehyde, vanillin isobutyrate, 2-phenyl-3-(2-furyl)prop-2-enal, ethyl vanillin acetate, vanillin acetate, heptanal, lauryl aldehyde, nonanal, octanal, phenylacetaldehyde, phenyl propyl aldehyde, salycil aldehyde, citral, 2,4-dihydroxy-3-methylbenzaldehyde, 2-hydroxy-4-methylbenzaldehyde, 5-methyl salicylic aldehydes, 4-nitrobenzaldehyde, o-nitrobenzaldehyde, 5-ethyl-2-thiophenecarbaldehyde, 2-thiophenecarbaldehyde, asaronaldehyde, 5-(hydroxymethyl)-2-furaldehyde, 2-benzofurancarboxaldehyde, 2,3,4-trimethoxybenzaldehyde, protocatechualdehyde, heliotropine, 4-ethoxy-3-methoxy benzaldehyde, 3,4,5-trimethoxybenzaldehyde, 3-hydroxybenzaldehyde, o-methoxycinnamaldehyde, 3,5-dimethoxy-4-hydroxycinnamaldehyde, 2,8-dithianon-4-3n-4-carboxaldehyde, sorbinaldehyde, 2,4-heptadienal, 2,4-decadienal, 2,4-nonadienal, 2,4-nonadienal, (E,E)-,2,4-octadien-1-al, 2,4-octadienal, 2,4-dodecadienal, 2,4-undecadienal, 2,4-tridecadien-1-al, 2-trans-4-cis-7-cis-tridecatrienal, piperonylidene propionaldehyde, 2-methyl-3-(2-furyl)acrolein, 2,4-pentadienal, 2-furfurylidene butyrraldehyde, helional, lyral, 3-hexenal, Safranal, veratraldehyde, 3-(2-furyl)acrolein, pyruvaldehyde, ethanedial, 1-(2,6,6-trimethyl-1-cyclohexenyl)pent-1-en-3-one; 4-(2,6,6-trimethyl-1-cyclohexen-1-yl)-3-Buten-2-one; 4-(2,6,6-trimethyl-2-cyclohexen-1-yl)-3-buten-2-one, 5-(2,6,6-Trimethyl-2-cyclohexen-1-yl)-4-penten-3-one, (E)-4-(2,2-dimethyl-6-methylidenecyclohexyl)but-3-en-2-one.

10. An absorbent article according to claim 1, further comprising one or more additional masking compounds in complexed or encapsulated form selected from: menthol, menthyl acetate, menthyl lactate, menthyl propionate, menthyl butyrrate, menthone, mint terpenes, laevo-carvone, Cis-3-Hexenol & Cis-3-Hexenyl acetate, koavone, methyl dioxolan.

11. An absorbent article according to claim 1, further comprising one or more additional malodor masking and fragrance compounds in complexed or encapsulated form selected from: methyl-dihydrojasmonate, methyl jasmonate, eucalyptol, tetrahydro-linalool, Phenyl-Ethyl alcohol, Hexyl iso-butyrate, Linalyl acetate, Benzyl acetate, benzyl alcohol, camphor, p-menthane, limonene, cresol, linalool, myrcenol, tetra hydromyrcenol, di-hydromyrcenol, myrcene, cytronellol, cytronellyil derivatives, geraniol, geranyl derivatives, mugetanol, eugenol, jasmal, terpineol, pinanol, cedrene, damascone, beta pinene, cineole and its derivatives, nonadienol, ethylhexanal, octanol acetate, methyl furfural, terpinene, thujene, amylacetate, camphene, citronellal, hydroxycitronellal, ethyl maltol, methyl phenyl carbinyl acetate, dihydrocumarin, dy hydromyrcenyl acetate, geraniol, geranial, isoamylacetate, ethyl, and/or triethyl acetate, para-cresol, para-cymene, methyl abietate, hexyl-2-methyl butyrate, and hexyl-2-methyl butyrate.

12. An absorbent article according to claim 1, wherein said one or more complexed or encapsulated compound has been prepared using a manufacturing process which includes a step in which said capsule or complex is spray dried.

13. An absorbent article according to claim 1, wherein said one or more complexed or encapsulated compound is applied to the article dispersed in a liquid carrier.

14. A method for reducing malodors associated with bodily fluids comprising the step of contacting said bodily fluid with an absorbent article according to claim 1.

15. A method for making an absorbent article including the step of applying at least two complexed or encapsulated compounds selected from: 3-(3-propan-2-ylphenyl)butanal, 2- methyl-3-[4-2-methylpropyl)phenyl]propanal, (3-(4-ethylphenyl)-2,2-dimethylpropanal), trans-2-hexanal, Floral Super, 5-methyl-2-thiophene-carboxaldehyde, hydratropic aldehyde, undecenal, 9-undecenal, trans-4-decenal, cis-6-nonenal, isocyclocitral, precyclemone b, (E)-2-(z)-6-nonadienal, undecyl aldehyde, silvial, vanillin, and floralozone.

16. An absorbent article comprising at least two complexed or encapsulated compounds selected from: trans-2-hexenal, undecenal, 9-undecenal, trans-4-decenal, cis-6-nonenal and (E)-2-(z)-6-nonadienal.

* * * * *